United States Patent [19]

Santa

[11] Patent Number: 5,989,571
[45] Date of Patent: Nov. 23, 1999

[54] CONTACT DERMATITIS PHARMACEUTICAL PREPARATION WITH ANTI-HISTAMINE AND ANTI-INFLAMMATORY

[75] Inventor: James E. Santa, Greeley, Colo.

[73] Assignee: Millenium Pharmaceutical Technologies, Inc., Greeley, Colo.

[21] Appl. No.: 08/899,287

[22] Filed: Jul. 23, 1997

[51] Int. Cl.$^6$ .................................................. A61K 6/00
[52] U.S. Cl. .............................. 424/401; 514/887
[58] Field of Search .............................. 424/401; 514/887

[56] References Cited

U.S. PATENT DOCUMENTS

| | | | |
|---|---|---|---|
| 4,137,311 | 1/1979 | Klein | 424/240 |
| 4,250,163 | 2/1981 | Nagai et al. | 424/14 |
| 4,419,352 | 12/1983 | Cox et al. | 424/248.4 |
| 5,013,545 | 5/1991 | Blackman et al. | 424/81 |
| 5,061,700 | 10/1991 | Dow et al. | 514/169 |
| 5,258,391 | 11/1993 | Van Scott et al. | 514/529 |
| 5,508,043 | 4/1996 | Krishnamurthy | 424/484 |
| 5,543,148 | 8/1996 | Lapidus | 424/401 |
| 5,547,988 | 8/1996 | Yu et al. | 514/557 |
| 5,602,193 | 2/1997 | Martin et al. | 514/724 |
| 5,622,993 | 4/1997 | McGinity | 514/626 |

FOREIGN PATENT DOCUMENTS

| | | | |
|---|---|---|---|
| 004119170A1 | 12/1992 | Germany | A61K 35/04 |
| 409110680 | 4/1997 | Japan | A61K 9/70 |
| 409157161 | 6/1997 | Japan | A61K 31/165 |

*Primary Examiner*—Thurman K. Page
*Assistant Examiner*—Todd D Ware
*Attorney, Agent, or Firm*—Gibson, Dunn & Crutcher LLP

[57] ABSTRACT

A pharmaceutical preparation, and treatment method using the same, for contact dermatitis and particularly for canine contact dermatitis. The preparation has as active ingredients an anti-histamine and an anti-inflammatory. The anti-histamine is preferably diphenhydramine. The anti-inflammatory is preferably triamcinolone. The preparation is a liquid mixture and is sprayed or otherwise applied onto an affected area.

7 Claims, No Drawings

CONTACT DERMATITIS PHARMACEUTICAL PREPARATION WITH ANTI-HISTAMINE AND ANTI-INFLAMMATORY

FIELD OF THE INVENTION

The invention relates to pharmaceutical preparations useful for treating contact dermatitis having both an anti-histamine and an anti-inflammatory and methods of using said compounds. In one embodiment, the preparation is a composition of diphenhydramine and triamcinolone for treating canine contact dermatitis.

BACKGROUND OF THE INVENTION

Human beings and most animals may suffer from a variety of skin irritations and inflammations generally known as dermatitis. Dogs in particular are prone to contact dermatitis caused by flea or other insect bites, allergies, external stimulation such as from prickly plants, and for other reasons. The condition has been notoriously difficult to treat. Veterinarians occasionally resort to injections of various medicines in an attempt to alleviate the symptoms and cure the dermatitis.

A number of topical compounds have been used for the treatment of skin conditions for many years. Such compounds have had only limited success in the treatment of canine contact dermatitis. Moreover, such compounds may be messy and/or noxious either to a dog or to a person applying the medicine.

It can be appreciated that a compound that is safe, effective, and easy to manufacture and apply will be a welcome advance in the treatment of contact dermatitis and other skin conditions.

SUMMARY OF THE INVENTION

The present invention is a pharmaceutical preparation (and method of using the same) intended for the treatment of contact dermatitis, and has been found to particularly effective for canine contact dermatitis.

The active ingredients are an anti-histamine, diphenhydramine, and an anti-inflammatory, triamcinolone. The preparation is a liquid and preferably sprayed onto the affected area.

DETAILED DESCRIPTION OF THE INVENTION

Dermatitis, an inflammation of the skin, afflicts humans and many animals and has a number of causes. Dogs in particular suffer from contact dermatitis, often caused by flea or other insect bites, allergies, external stimulation such as prickly plants, and for other reasons. While the condition may be cured by natural healing processes, the condition may cause such discomfort that medication is desirable.

The invention includes a pharmaceutical preparation having active ingredients of an anti-histamine and an anti-inflammatory agent, and a method of using the composition to treat contact dermatitis. The preparation has been found to be particularly effective in treating canine contact dermatitis.

The preferred anti-inflammatory is triamcinolone. It is preferably supplied as triamcinolone acetonide, and a commercial preparation known to be effective in the invention has a concentration of 1 mg/ml in a lotion base of propylene glycol, cetyl alcohol, stearyl alcohol, sorbitan monopalmitate, polysorbate 20, simethicone, and purified water (TAC Lotion (NDC 0364-7346-58) available from Schein Pharmaceutical Inc. of Furham Park, N.J.). Triamcinolone reduces further inflammatory response and is used in different forms for the treatment of contact dermatitis in humans. Its use as a veterinary pharmaceutical is unknown to the inventor.

The preferred anti-histamine is diphenhydramine, commonly used for the treatment of allergies or for cough and common cold symptoms. For the present invention, it is most preferably supplied as an elixir having a concentration of 12.5 mg/5 cc in an elixir base of citric acid, D&C red #33, Fdc Red #40, flavors, glycerine, poloxamer 407, polysorbate 20, sodium benzoate, sodium citrate, sodium saccharin, sugar, and water (available as NDC 12333-9072-2).

The preferred preparation is a mixture of equal parts of the above diphenhydramine and triamcinolone compounds. The mixture creates a suspension that stays well mixed for short period of time (such as the time necessary to prepare and apply to an animal). The mixture should be shaken before application. While a mixture of equal parts is presently preferred, it can be expected that other mixtures may have similar therapeutic effects, particularly within the range of between 25% and 75% of diphenhydramine and the remainder of triamcinolone.

The preparation admits the use of regular light- and air-tight containers as are commonly used to store liquid medicines. An effective bottle is a prescription bottle of between two and four ounces, amber color, and has a spray applicator. Alternatively, the preparation may be applied by other means such as by being rubbed onto an affected area.

The preparation is used to treat canine contact dermatitis as follows. The affected area should be relatively dry. The bottle containing the preparation is well shaken and placed with the spray applicator about six to eight inches from the area. The preparation is sprayed onto the area until saturated. The preparation can be rubbed into the affected area, but that is generally not necessary. Preferably, the dog is engaged for several minutes (for example, from three to five minutes) after the application so that it will not lick or otherwise disturb the affected area. Feeding the animal is one effective stratagem. It can be readily understood that the preparation can be used to treat dermatitis and other skin conditions, in humans and animals, in the same manner.

The preparation is preferably applied either once or twice daily, until the condition is resolved. It has been observed that relief is usually obtained within several days to several weeks.

While not being bound to any particular scientific theory or understanding, it is believed that the diphenhydramine alleviates the discomfort associated with the dermatitis, allowing for the triamcinolone to stabilize cell membranes and treat the underlying condition. The preparation and treatment method have been found to be particularly effective in the treatment of canine dermatitis. It is expected that the preparation and treatment method may be effective to treat contact dermatitis for humans and other animals, and may also be effective for the treatment of minor burns and other skin afflictions. It will be appreciated that the invention may be modified without departing from the spirit and scope of the invention as a whole.

What is claimed is:

1. A pharmaceutical preparation for the treatment of dermatitis, comprising as active ingredients an anti-histamine and an anti-inflammatory, wherein the anti-histamine is diphenhydramine in the form of an elixir and the anti-inflammatory is triamcinolone and the preparation is in the form of a liquid suspension, wherein the active ingredients are present in a therapeutically effective amount.

2. A pharmaceutical preparation according to claim 1, wherein the diphenhydramine is a compound having a concentration of about 12.5 mg/5 cc and the triamcinolone is a compound having a concentration of about 1 mg/ml.

3. A pharmaceutical preparation according to claim 2, wherein the preparation has is between about 25% and 75% of the diphenhydramine compound and the remainder is the triamcinolone compound.

4. A pharmaceutical preparation according to claim 3, wherein the preparation has equal parts of the diphenhydramine compound and the triamcinolone compound.

5. A treatment method for dermatitis, comprising applying directly to an affected area a liquid preparation having as active ingredients an anti-histamine and an anti-inflammatory, wherein the preparation has as active ingredients diphenhydramine in the form of an elixir and triamcinolone and the preparation is in the form of a liquid suspension, wherein the active ingredients are present in a therapeutically effective amount.

6. A treatment method according to claim 5, wherein the diphenhydramine is a compound having a having a concentration of about 12.5 mg/5 cc and the triamcinolone is a compound having a concentration of about 1 mg/ml.

7. A treatment method according to claim 6, wherein the preparation has equal parts of the diphenhydramine compound and the triamcinolone compound.

* * * * *